United States Patent [19]

Habermeier

[11] 4,130,560

[45] Dec. 19, 1978

[54] DICARBOXYLIC ACID DERIVATIVES CONTAINING HETEROCYCLIC RADICALS

[75] Inventor: Jürgen Habermeier, Pfeffingen, Switzerland

[73] Assignee: Ciba-Geigy Corporation, Ardsley, N.Y.

[21] Appl. No.: 633,772

[22] Filed: Nov. 20, 1975

[30] Foreign Application Priority Data

Nov. 29, 1974 [CH] Switzerland ............... 18565/74

[51] Int. Cl.² ............ C07D 239/52; C07D 239/64; C07D 233/72; C07D 233/96; C09K 5/06
[52] U.S. Cl. ................................ 544/302; 548/305; 548/307; 548/310; 548/321; 528/289; 528/341; 528/367; 544/301; 544/312; 544/314
[58] Field of Search ............ 260/260, 309.2, 309.8, 260/257, 309.7, 309.5

[56] References Cited

FOREIGN PATENT DOCUMENTS 622301  6/1961  Canada ........................... 260/309.2

*Primary Examiner*—Natalie Trousof
*Assistant Examiner*—Cary Owens
*Attorney, Agent, or Firm*—Luther A. R. Hall

[57] ABSTRACT

New dicarboxylic acid derivatives containing a N,N-heterocyclic radical are obtained by reacting 1 mol of a cyclic ureide, such as 1,1-methylene-bis-hydantoin, benzimidazolone, parabanic acid, 6-methyluracil or 2,2-diethylbarbituric acid, with 2 mols of 4-halogenomethylbenzoic acid derivatives. The new dicarboxylic acid derivatives are valuable monomers for the manufacture of stable plastics. Thus, the dicarboxylic acid dialkyl esters, for example, can be converted by means of diols into polyesters with valuable mechanical properties.

10 Claims, No Drawings

DICARBOXYLIC ACID DERIVATIVES CONTAINING HETEROCYCLIC RADICALS

The present invention relates to new dicarboxylic acid derivatives containing a N,N-heterocyclic radical and to a process for their manufacture.

Dicarboxylic acids which contain a N,N-heterocyclic radical in the molecule are already known. Thus "Chemical Abstracts", Volume 59, page 3907(e), describes the manufacture of dicarboxylic acids containing hydantoin and alkylene-bis-hydantoins by cyanoethylation of hydantoin and alkylene-bis-hydantoins and subsequent hydrolysis of the resulting cyanoethyl compounds to give dicarboxylic acids. However, these dicarboxylic acids suffer from the disadvantage that they do not have a high heat stability and readily redissociate into the hydantoin compounds and acrylic compounds on being further processed while hot, for example in the manufacture of polyesters by the melt condensation process.

DT-OS 1,906,492 also describes the manufacture of oligo-hydantoins and poly-hydantoins containing carboxylic acid functions by reacting polyglycine esters with isocyanates containing carboxylic acid functions. This manufacturing process suffers from the disadvantage that, on the one hand, the starting materials which are necessary for it are only obtained via involved syntheses and, on the other hand, the reaction of the polyglycine esters with the isocyanates, which results in cyclisation, requires relatively high temperatures and the desired substances have to be separated from products in the reaction mixture, which have not been quantitatively cyclised.

In the case of the dicarboxylic acid derivatives containing the triketomidazolidine ring, which can be manufactured from diisocyanates and N-(p-carboxyethylphenyl)oxamic acid alkyl esters in accordance with the process disclosed in DT-OS 1,916,932 the synthesis also proceeds via a cyclisation which can only be carried out reasonably well in thin layers. Furthermore, the dicarboxylic acids and derivatives thereof are obtained in a state of inadequate purity by these syntheses.

It has now been found that dicarboxylic acid derivatives containing a N,N-heterocyclic radical can be obtained in a simpler manner if cyclic ureides which have a symmetrical structure are reacted with 4-halogenomethylbenzoic acid derivatives.

The present invention therefore relates to new dicarboxylic acid derivatives, containing a N,N-heterocyclic radical, of the formula I

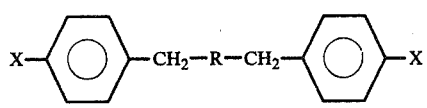

(I)

wherein each X denotes a nitrile group or an alkoxycarbonyl group having 1-12 C atoms and R denotes a divalent N,N-heterocyclic radical of the formulae

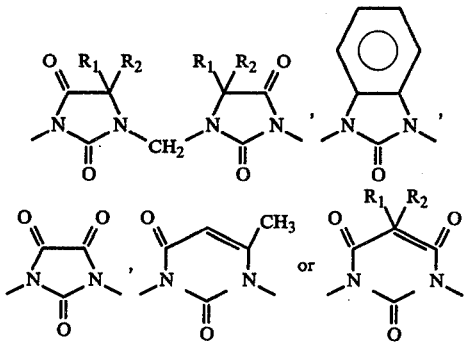

wherein $R_1$ and $R_2$ independently of one another each denote a hydrogen atom or an alkyl group having 1 to 3 C atoms.

In the formula I, each X preferably denotes a methoxycarbonyl or ethoxycarbonyl group and R denotes a divalent N,N-heterocyclic radical of the formula

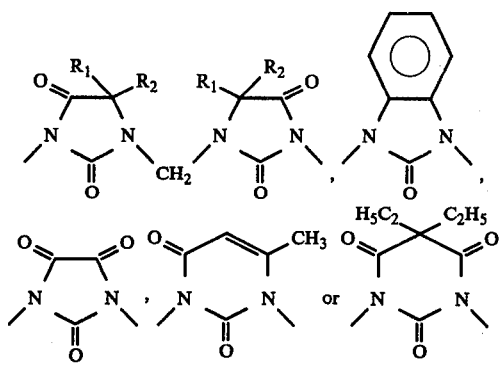

wherein $R_1$ and $R_2$ have the same meaning as in the formula I.

In particular, each X in the formula I denotes a methoxycarbonyl or ethoxycarbonyl group and R denotes the N,N-heterocyclic radical of the formula

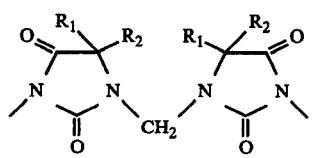

wherein $R_1$ and $R_2$ have the same meaning as in formula I.

The new dicarboxylic acid derivatives, containing a N,N-heterocyclic radical, of the formula I are obtained by reacting 1 mol of a N,N-heterocyclic compound of the formula

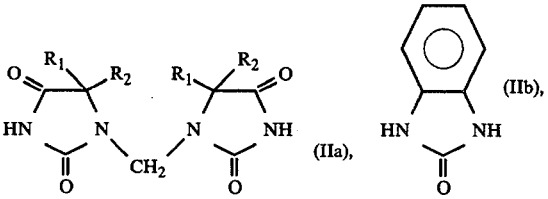

-continued

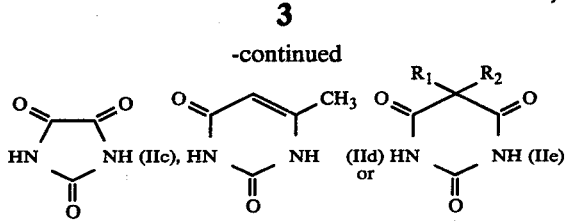

or of the disodium salts thereof, with 2 mols of a compound of the formula III

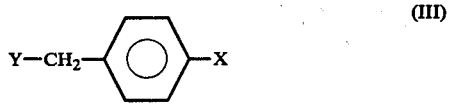

(III)

wherein X has the same meaning as in the formula I and Y represents chlorine or bromine, with the elimination of 2 mols of hydrogen chloride or hydrogen bromide, or sodium chloride or sodium bromide, respectively, to give compounds of the formula I.

The compounds of the formulae II used in this process are preferably 1,1,'-methylene-bis-hydantoin unsubstituted or substituted in the 5-position, benzimidazolone, parabanic acid, 6-methyluracil or 2,2-diethylbarbituric acid, and these are preferably reacted with those compounds of the formula III wherein X denotes a methoxycarbonyl or ethoxycarbonyl group and Y represents, in particular, chlorine. In particular, 1,1'-methylene-bis-hydantoin, unsubstituted or substituted in the 5-position, is used here.

As a rule the conversion reaction is carried out in a polar, aprotic solvent, such as dimethylformamide, dimethylacetamide, hexamethylphosporic acid triamide or dioxane. It is also possible to carry out the conversion reaction without a solvent, that is to say in the melt. If the cyclic ureides of the formulae IIa to IIe are used as the starting substance, 1 mol of the chlorine-containing compound of the formula III, preferably a slight molar excess of the compound of the formula III, is employed per 1 equivalent of reactive NH group. The reaction, which takes place with the elimination of hydrogen halide, is appropriately carried out in the presence of an acid acceptor, which is added to the solvent in quantities corresponding at least to equivalent quantities, relative to the calculated quantity of hydrogen halide liberated. Suitable acid acceptors for this purpose are, in particular, ground, anhydrous potassium carbonate or sodium carbonate. Furthermore, sodium ethylate or sodium methylate or sodium hydroxide powder are also suitable. The conversion reaction is carried out at temperatures between 50 and 180° C, preferably at 60 to 140° C.

The reaction product is isolated by filtering the reaction solution, while hot, in order to remove the potassium halide which is formed when using potassium carbonate, for example, as the acid acceptor, and the desired product is obtained by allowing it to crystallise out from the reaction solution or by pouring the mixture into water and precipitating it, or by concentrating the reaction solution to dryness and recrystallising the crude product in an organic solvent. Various organic solvents, such as, for example, methanol, acetone, ethanol or tetrahydrofuran, are suitable for this purpose.

When the N,N-heterocyclic compounds of the formulae II are used in the form of their di-sodium salts, the latter are first rendered anhydrous by thorough drying and are then appropriately also suspended in a polar, aprotic solvent, 2 to 2.2 mols of a compound of the formula III being employed per 1 mol of the disodium salt of a compound of the formula II. The reaction can take place at temperatures between 20 and 180° C. The conversion reaction is preferably carried out within the temperature range from 60 to 140° C. The reaction solution is then worked up in the same way as described above.

The N,N-heterocyclic compounds of the formulae IIa to IIe are known compounds, namely 1,1'-methylene-bis-(hydantoin) unsubstituted or substituted in the 5-position by lower alkyl groups, such as methyl, ethyl or isopropyl groups (IIa), benzimidazolone (IIb), parabanic acid (IIc) 6-methyluracil (IId) and barbituric acid (IIe), unsubstituted or substituted by alkyl in the 5-position.

The compounds of the formula III are also known from the literature and can be obtained, for example, by the process described in DT-AS 1,001,253 by direct chlorination of 4-methylbenzoic acid derivatives in the side chain. Another possible means of manufacturing compounds of the formula III consists in photochlorinating 4-methylbenzoic acid derivatives in a suitable solvent by the process described in DT-AS 1,929,743.

The new dicarboxylic acid derivatives containing a N,N-heterocyclic radical are colourless, crystalline substances which melt between 50 and 250° C and are readily soluble in organic solvents, but are insoluble, or only very slightly soluble, in water.

The new dicarboxylic acid derivatives are valuable monomers which are suitable for the manufacture of heat-stable plastics. Thus, for example, the dicarboxylic acid dialkyl esters or the dicarboxylic acids which can be manufactured from them, can be converted by means of diols into polyesters which have very valuable mechanical properties. The diglycidyl esters obtained from the dicarboxylic acids by glycidylation using an epilhalogenohydrin, can also be cured to give epoxide resins with valuable mechanical properties.

The dinitriles manufactured in accordance with the invention are, in turn, suitable for the manufacture of the corresponding dicarboxylic acids and for the manufacture of diprimary amines which are of interest as curing agents for epoxide reins.

EXAMPLE 1

1,1'-Methylene-bis-[3-(4'-methoxycarbonylbenzyl)-5,5-dimethylhydantoin]

67.1 g (0.25 mol) of 1,1'-methylene-bis-(5,5-dimethylhydantoin), 96.9 g (0.525 mol) of 4-chloromethylbenzoic acid methyl ester and 38 g (0.275 mol) of finely powdered, anhydrous potassium carbonate in 450 ml of dimethylformamide are initially introduced into a glass apparatus provided with a reflux condenser, a thermometer and a stirrer. The mixture is warmed at 120° C for five hours while stirring vigorously.

The reaction mixture is filtered while hot. The filtrate obtained is concentrated to 280 ml and cooled to 5° C. The crystals which are precipitated are isolated by filtration and dried to constant weight at 70° C in a vacuum oven.

This gives 122.5 g (86.8% of theory) of a colourless, crystalline powder.

The product is purified by recrystallisation from methanol. This gives 98.8 g (70% of theory) of colourless, glittering crystals, which melt at 145–147° C and of which a micro-analysis gives the following result:

| Found | Calculated (for $C_{29}H_{32}N_4O_8$) |
|---|---|
| 61.79% C | 61.69% C |
| 5.61% H | 5.71% H |
| 9.90% N | 9.92% N |

The proton magnetic resonance spectrum (H-NMR) also shows that the compound has the following structure.

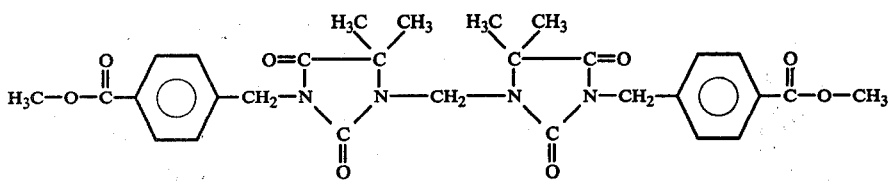

If the product obtained is purified by recrystallisation, not from methanol, but from acetone, a very pure product is also obtained which, however, according to C, H, N analysis and H-NMR spectrum, contains about 1 mol of acetone of crystallisation per mole of substance; the melting point of this substance is 111–112° C (with decomposition).

EXAMPLE 2

1,1'-Methylene-bis-[3-(4'-methoxycarbonylbenzyl)-5,5-dimethylhydantoin]

A mixture of 31.2 g (0.1 mol) of disodium 1,1'-methylene-bis-(5,5-dimethylhydantoin) and 38.7 g (0.21 mol) of 4-chloromethylbenzoic acid methyl ester in 180 ml of N,N-dimethylformamide is stirred at room temperature (23° C). A mildly exothermic reaction takes place and the reaction mixture warms up to 33° C over the course of 45 minutes. After this exothermic reaction has subsided, the mixture is warmed to 120° C over the course of 4½ hours while stirring vigorously. The product is isolated in accordance with Example 1. Purification is also carried out by recrystallisation from methanol.

This gives 40.3 g (71.3% of theory) of the desired pure product, which melts at 146–147° C and is identical with the product described in Example 1.

EXAMPLE 3

1,3-Di-(4'-methoxycarbonylbenzyl)-benzimidazolone

The following mixture of substances is reacted in 800 ml of dimethylformamide as described in Example 1: 61.15 g (0.456 mol) of benzimidazolone, 176.6 g (0.957 mol) of 4-chloromethylbenzoic acid methyl ester and 69.1 g (0.5 mol) of finely powdered, anhydrous potassium carbonate.

76.5 g of the desired product (39% of theory) are obtained after carrying out the reaction and working up in accordance with Example 1. Recrystallisation from 600 ml of dioxane gives the new product (66.2 g) as a colourless, crystalline powder which melts at 209–211° C. Elementary analysis gives:

| Found: | Calculated (for $C_{25}H_{22}N_2O_5$) |
|---|---|
| 69.6% C | 69.76% C |
| 5.1% H | 5.15% H |
| 6.6% N | 6.51% N |

The H-NMR spectrum also accords with the following structure:

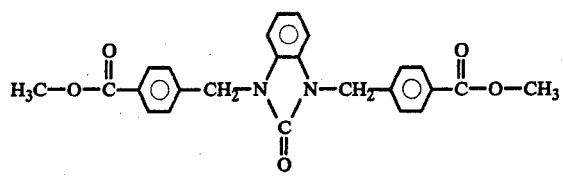

EXAMPLE 4

1,3-Di-(4'-methoxycarbonylbenzyl)-5,5-diethylbarbituric acid

A mixture of 46.05 g (0.25 mol) of diethylbarbituric acid, 96.9 g (0.525 mol) of 4-chloromethylbenzoic acid methyl ester and 38 g (0.275 mol) of finely ground, anhydrous potassium carbonate in 450 ml of dimethylformamide is stirred at room temperature and is heated to 100° C over the course of 2 hours. The reaction solution is kept at 100° C for one hour and the temperature is then raised to 135° C, whilst stirring. Stirring is continued for a further 4 hours at 135° C and the reaction mixture is then filtered, while still hot. 77.8 g of colourless crystals can be isolated from the cooled filtrate and concentrating the mother liquor gives a further 42 g of a syrup which crystallises (total yield of crude material: 119.8 g; theory: 120.1 g).

The product can be purified by recrystallisation from dioxane (77.8 g in 270 ml of dioxane). This gives colourless crystals (67.9 Δ 72%) of melting point 190–191° C. Elementary analysis gives, for $C_{26}H_{28}N_2O_7$:

| Found | Calculated: |
|---|---|
| 65.0% | 64.99% C |
| 6.0% H | 5.87% H |
| 5.8% N | 5.83% N |

The product thus obtained is a single substance according to thin layer chromatographic analysis and its H-NMR spectrum accords with the following structure.

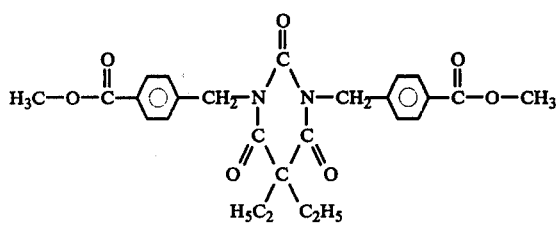

EXAMPLE 5

1,1'-Methylene-bis-[3-(4'-methoxycarbonylbenzyl)-5,5-dimethylhydantoin]

The process described in Example 1 is altered in that the water formed in the reaction is continuously removed from the mixture in order to repress side-reactions and to improve the yield.

For this purpose the following procedure is adopted: a mixture of 80.4 g (0.3 mol) of 1,1'-methylene-bis-(5,5-dimethylhydantoin), 144.9 g (0.63 mol) of p-chloromethylbenzoic acid methyl ester, 45.6 g (0.33 mol) of dried, pulverised potassium carbonate, 400 ml of dimethylformamide and 400 ml of benzene is reacted at 94–96° C for 5 hours, while stirring, in a glass apparatus equipped with a water separator, and the water present in the reaction mixture is continuously removed from the mixture by azeotropic distillation and is separated off. Working up is carried out as described in Example 1. 149.5 g of colourless crystals (88.1% of theory) of melting point 141–144° C are obtained. The product can be purified as described in Example 1; the analytically pure product is then obtained in a 72.1% yield.

EXAMPLE 6

1,3-Di-(4'-methoxycarbonylbenzyl)-6-methyluracil 48.3 g (0.21 mol) of 4-chloromethylbenzoic acid methyl ester are condensed by the process described in Example 5 with 12.6 g (0.1 mol) of 6-methyluracil in a mixture of 150 ml of benzene and 150 ml of dimethylformamide, using 15.2 g of dry potassium carbonate powder as the hydrochloric acid acceptor. The mixture is stirred for 10 hours while removing the water formed and the reaction mixture is then filtered while hot. The light yellow solution is concentrated completely, 43 g of a light yellow, crystalline mass being formed (yield of crude material 100% of theory). The product is purified by precipitation from methanol/petroleum ether and then by recrystallisation from methanol/ether. This gives virtually colourless crystals which melt at 156–158° C.

The thin layer chromatogram shows that this product is a single substance. Elementary analysis gives, for $C_{23}H_{22}N_2O_6$

| Found: | Calculated: |
|---|---|
| 6.60% N | 6.63% N |
| 5.20% H | 5.25% H |

The H-NMR spectrum (60 Mc; recorded in $CDCl_3$) is also in accord with the following structure:

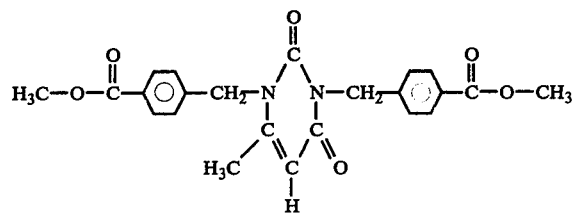

EXAMPLE 7

1,3-Di-(4'-methoxycarbonylbenzyl)-parabanic acid

If the 6-methyluracil in Example 6 is replaced by 11.9 g of 96% strength parabanic acid (0.1 mol) and if the procedure is exactly in accordance with Example 6, 42 g of a light brown crystal mash (100% of theory) are obtained as the crude product. This product can be purified by recrystallisation from dioxane-methanol. This gives the pure product in the form of pale yellow crystals.

The product melts at 192.5–193.2° C and combustion analysis gives, for $C_{21}H_{18}N_2O_7$:

| Found: | Calculated: |
|---|---|
| 61.20% C | 61.46% C |
| 4.50% H | 4.42% H |
| 7.00% N | 6.83 |

The N-NMR spectrum proves the presence of the following structure:

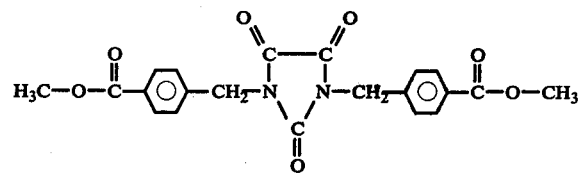

EXAMPLE 8

1,1'-Methylene-bis-[3-(4'-ethoxycarbonylbenzyl)-5,5-dimethylhydantoin]

26.8 g (0.1 mol) of 1,1'-methylene-bis-(5,5-dimethylhydantoin) are condensed by the process described in Example 5 with 46.1 g (0.21 mol) of 90.6% strength 4-chloromethylbenzoic acid ethyl ester in 200 ml of a 1:1 mixture of dimethylformamide and benzene, under the neutralising action of 16.6 g (0.12 mol) of dry potassium carbonate powder; the mixture is allowed to react for 4 hours while removing water from the system. Working up is carried out in accordance with Example 5 and 50.5 g of the crude product melting at 122–126° C are obtained (85.2% of theory). The latter is purified by recrystallisation from 150 ml of ethanol. This gives 46.3 g of the colourless, crystalline, analytically pure product (78% of theory) which melts at 129–131° C. Combustion analysis gives, for $C_{31}H_{36}N_4O_8$:

| Found: | Calculated: |
|---|---|
| 62.60% C | 62.83% C |
| 6.10% H | 6.12% H |
| 9.50% N | 9.45% N |

The thin layer chromatogram shows that the product is a single substance and the H-NMR spectrum is in accord with the following structure:

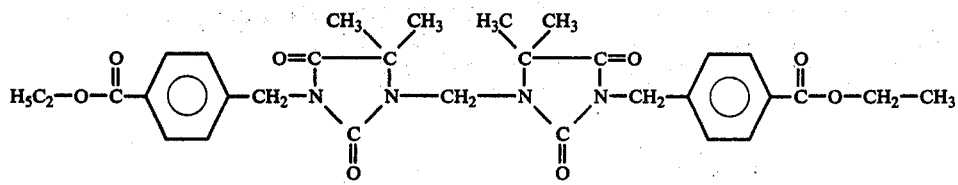

EXAMPLE 9

1,1′-Methylene-bis-[3-(4′-cyanobenzyl)-5,5-dimethylhydantoin]

251.9 g (0.94 mol) of 1,1′-methylene-bis-(5,5-dimethylhydantoin) are reacted, in accordance with Example 5, with 299.8 g (1.975 mols) of 4-chloromethylbenzonitrile, a mixture of 1,300 ml of dimethylformamide and 1,300 ml of benzene being used as the reaction medium and 143.1 g (1.039 mols) of dry potassium carbonate powder being used to take up the hydrochloric acid formed. This mixture is stirred for 6 hours at 93–95° C and the water formed in the neutralisation is continuously removed by azeotropic distillation.

Working up as described in Example 5 gives 414.3 g (88.4% of theory) of colourless crystals which melt at 207–209° C. The product can be purified further by recrystallisation from dioxane/chloroform (9:1). This gives 408.9 g (87.3% of theory) of the analytically pure product in the form of colourless crystals. The purified product melts at 208.6–209.5° C. The thin layer chromatogram shows that the product is a single substance and the H-NMR spectrum proves the presence of the structure shown below. Elementary analysis gives, for $C_{27}H_{26}N_6O_4$:

| Found: | Calculated |
|---|---|
| 61.10% C | 65.05% C |
| 5.20% H | 5.26% H |
| 16.90% N | 16.86% N | tassium carbonate powder are used to take up the hydrochloric acid formed.

This mixture is stirred for 4 hours at an internal temperature of 96–98° C, and the water formed in the neutralisation is removed from the mixture by azeotropic circulatory distillation. After completion of the reaction, the solution is filtered while it is still hot and is concentrated to dryness in vacuo.

59.2 g of a solid, yellowish resin (100% of theory) are obtained as a crude product. This product can be purified by recrystallisation from a 10-fold quantity of methanol. This gives 37.5 g (63.4% of theory) of colourless crystals which melt at 147.5–149.5° C.

The H-NMR spectrum is in accord with the structure shown below. Combustion analysis gives, for $C_{31}H_{36}N_4O_8$:

| Found: | Calculated: |
|---|---|
| 62.45% C | 62.83% C |
| 6.10% H | 6.12% H |
| 9.42% N | 9.45% N |

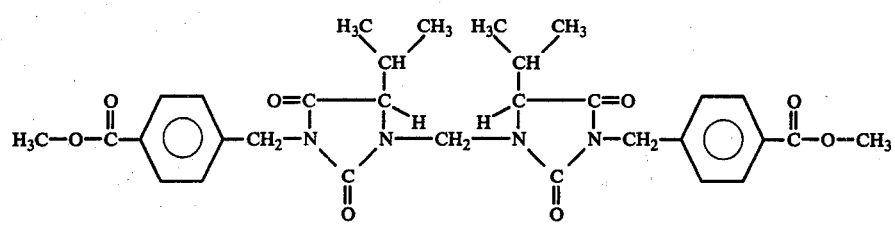

APPLICATION EXAMPLE

Homopolyester formed from the product obtained in accordance with Example 1 and ethylene glycol.

The mixture which follows is subjected to transesterification and polycondensation under the conditions indicated below in a glass apparatus provided with a thermometer, a descending condenser, a stirrer and a nitrogen inlet:

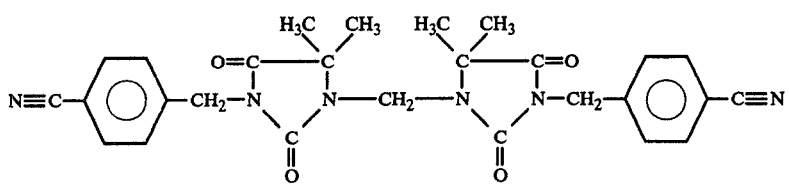

EXAMPLE 10

1,1′-Methylene-bis-[3-(4′-methoxycarbonylbenzyl)-5-isopropylhydantoin]

29.6 g (0.1 mol) of 1,1′-methylene-bis-(5-isopropylhydantoin) are condensed, analogously to Example 5, with 38.6 g (0.21 mol) of 4-chloromethylbenzoic acid methyl ester in a mixture of 150 ml of benzene and 150 ml of dimethylformamide. 15.2 g (0.11 mol) of dry po- 50.8 g (0.09 mol) of 1,1′-methylene-bis-[3-(4′-methoxycarbonylbenzyl)-5,5-dimethylhydantoin] (according to Example 1), 27.9 g (0.45 mol) of ethylene glycol, 0.03 g of calcium acetate, 0.04 g of zinc acetate and 0.1 g of antimony trioxide.

2 hours / 160° C  →  210° C / N₂ / normal pressure

-continued

| 1.5 hours / 210° C | → 245° C / N₂ / normal pressure |
| 1.5 hours / 245° C | → 260° C / N₂ / 760 mm Hg → 16 mm Hg |
| 10 minutes / 260° C | / N₂ / 16 mm Hg → 0.4 mm Hg |
| 30 minutes / 260° C | → 280° C / N₂ / 0.4 mm Hg |

This gives a glass-clear, amorphous polyester which has a softening point (by Kofler's method) of 225° C and a relative viscosity (1% strength solution in tetrachloroethane/phenol = 1/1, measured at 30° C) of 1.63. The glass transition range (DSC-2B)* is 147–155° C; the decomposition temperature (DSC-2B) is about 330° C.
*)Differential Scanning Calorimeter 2B

I claim:

1. A compound of formula I

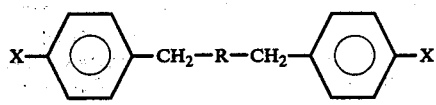

wherein each X denotes a nitrile group or alkoxycarbonyl group having 1 to 12 C atoms and R denotes a divalent N,N-heterocyclic radical of the formula

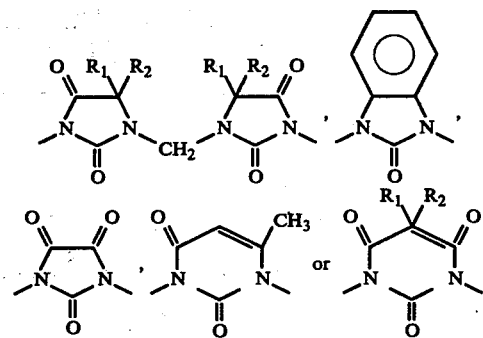

wherein $R_1$ and $R_2$ independently of one another each denote a hydrogen atom or an alkyl group having 1 to 3 C atoms.

2. A compound according to claim 1, wherein, in the formula I, each X denotes a methoxycarbonyl or ethoxycarbonyl group and R denotes a divalent N,N-heterocyclic radical of the formula

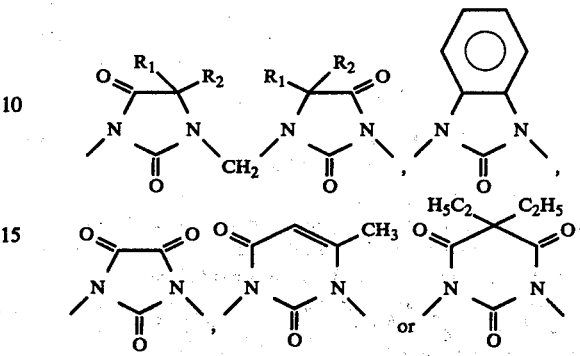

wherein $R_1$ and $R_2$ have the same meaning as in formula I.

3. A compound according to claim 1, which is 1,1'-methylene-bis-[3-(4'-methoxycarbonylbenzyl)-5,5-dimethylhydantoin].

4. A compound according to claim 1, which is 1,1'-methylene-bis-[3-(4'-ethoxycarbonylbenzyl)-5,5-dimethylhydantoin].

5. A compound according to claim 1, which is 1,1'-methylene-bis-[3-(4'-methoxycarbonylbenzyl)-5-isopropylhydantoin].

6. A compound according to claim 1, which is 1,3-di-(4'-methoxycarbonylbenzyl)-benzimidazolone.

7. A compound according to claim 1, which is 1,3-di-(4'-methoxycarbonylbenzyl)-6-methyluracil.

8. A compound according to claim 1, which is 1,3-di-(4'-methoxycarbonylbenzyl)-parabanic acid.

9. A compound according to claim 1, which is 1,3-di-(4'-methoxycarbonylbenzyl)-5,5-diethylbarbituric acid.

10. A compound according to claim 1, which is 1,1'-methylene-bis-[3-(4'-cyanobenzyl)-5,5-dimethylhydantoin].